US006518260B1

(12) United States Patent
Fournie-Zaluski et al.

(10) Patent No.: US 6,518,260 B1
(45) Date of Patent: Feb. 11, 2003

(54) (α-AMINOPHOSPHINO) PEPTIDE DERIVATIVES, METHOD FOR MAKING SAME AND THERAPEUTIC APPLICATIONS THEREOF

(75) Inventors: Marie-Claude Fournie-Zaluski, Paris (FR); Huixiong Chen, Bagneux (FR); Bernard Pierre Roques, Paris (FR)

(73) Assignee: Institut National de la Sante et de la Recherche Medicale (Inserm), Paris (FR)

( * ) Notice: Subject to any disclaimer, the term of this patent is extended or adjusted under 35 U.S.C. 154(b) by 0 days.

(21) Appl. No.: 09/284,882

(22) PCT Filed: Oct. 21, 1997

(86) PCT No.: PCT/FR97/01884

§ 371 (c)(1),
(2), (4) Date: Apr. 22, 1999

(87) PCT Pub. No.: WO98/18803

PCT Pub. Date: May 7, 1998

(30) Foreign Application Priority Data

Oct. 25, 1996 (FR) ............................................ 96 13082

(51) Int. Cl.⁷ ..................... A61K 31/66; A61K 31/662; C07F 9/30; C07F 9/32
(52) U.S. Cl. ......................... 514/141; 514/75; 514/120; 562/8
(58) Field of Search ............................... 562/8; 514/75, 514/2, 141, 120

(56) References Cited

FOREIGN PATENT DOCUMENTS

| EP | 0 725 075 | 8/1996 |
|---|---|---|
| WO | WO 91/02718 | 3/1991 |
| WO | WO 95/35302 | 12/1995 |

OTHER PUBLICATIONS

S. Chackalamannil et al., "Highly Potent and Selective Inhibitors of Endothelin Converting Enzyme", Bioorganic & Medicinal Chemistry Letters, vol. 6, No. 11, pp. 1257–1260, (1996).

J. Jiráček et al., "Development of the First Potent and Selective Inhibitor of the Zinc Endopeptidase Neurolysin Using a Systematic Approach Based on Combinatorial Chemistry of Phosphinic Peptides", Journal of Biological Chemistry, vol. 271, No. 32, pp. 19606–19611, (1996).

D. Grobelny, "Binding Energetics of Phosphorus–Containing Inhibitors of Thermolysin", Biochemistry, vol. 28, No. 12, pp. 4948–4951, (1989).

B. P. Morgan et al., "Differential Binding Energy: A Detailed Evaluation of the Influence of Hydrogen–Bonding and Hydrophobic Groups on the Inhibition of Thermolysin by Phosphorus–Containing Inhibitors", Journal of the American Chemical Society, vol. 113, pp. 297–307, (1991).

K. M. Merz, Jr., et al., "Free Energy Perturbation Simulations of the Inhibition of Thermolysin: Prediction of the Free Energy of Binding of a New Inhibitor", Journal of the American Chemical Society, vol. 111, No. 15, pp. 5649–5658, (1989).

*Primary Examiner*—Michael Borin
(74) *Attorney, Agent, or Firm*—Young & Thompson

(57) ABSTRACT

The invention concerns compounds derived from (α-aminophosphino) peptides, of general formula (I), in which $R_1$ and $R_2$ each represents a hydrogen atom or taken together form an imine with the adjacent nitrogen atom; $R_3$ represents an alkyl group, an alkenyl group, a phenyl group, a benzyl group, all these groups capable of being substituted or not, a hydrogen atom, a cycloalkyl group, a cycloalkylmethyl group or finally, a methyl group substituted by a heterocyclic, aromatic or saturated group; $R_4$ represents a phenyl group, a benzyl group, these groups capable of being substituted or not, a hydrogen atom, an alkyl group, analkenyl group or a cycloalkyl group; $R_5$ represents an alkyl group, an alkenyl group, a phenyl group, a benzyl group, all these groups capable of being substituted or not, a hydrogen atom, a cycloalkyl, cycloalkylmethyl group or finally a methyl group substituted by a heterocyclic, aromatic or saturated group; $R_6$, $R_7$ and $R_8$ can in particular represent a hydrogen atom, an alkyl group, a phenyl group substituted or not . . . n is equal to 0 or 1, in the form of enantiomers, diastereoisomers or racemic mixtures, their salts, their method of preparation and their therapeutic applications.

6 Claims, No Drawings

(α-AMINOPHOSPHINO) PEPTIDE DERIVATIVES, METHOD FOR MAKING SAME AND THERAPEUTIC APPLICATIONS THEREOF

Novel (α-aminophosphino)peptide derivatives, process for their preparation and their therapeutic applications The perception, transmission and regulation of nociceptive influxes come under the influence of several endogenous neurotransmitters. In 1975, Hugues et al., *Nature,* 258, 577, 1975 revealed the enkephalins, two pentapeptides originally isolated from mammalian brains, which are involved in the transmission of pain influxes. Enkephalins are associated with at least two classes of receptors: the $\mu$ and $\delta$ opioid sites (Pert, *Sciences,* 179, 1011, 1973) whose roles and locations are different. Their antinociceptive properties have been demonstrated by Belluzi et al., *Nature,* 260, 625, 1976. However, the analgesia induced by the administration of exogenous enkephalins is very fleeting, on account of the rapid metabolization of these peptides. Enkephalin analogues made resistant to enzymatic degradation by chemical modifications have been synthesized, but their side effects are similar to those of morphine.

Enkephalins are physiologically degraded by two types of enzymatic activities which metabolize enkephalins in vivo: neutral endopeptidase (EC 3.4.24.11, also known as NEP) which cleaves the $Gly^3$-$Phe^4$ bond, and aminopeptidase N (EC 3.4.11.2, also known as APN) which cleaves the $Tyr^1$-$Gly^2$ bond (review in Roques et al., *Pharmacol. Rev.,* 45, 87–146, 1993).

Prodrugs which possess analgesic and antidepressant activities after intravenous or oral administration (Noble et al., *J. Pharm. Exp. Ther.,* 261, 181, 1992; Baamonde et al., *Eur. J. Pharmacol.,* 216, 157, 1992) are known, these being described in European patent EP 0,487,620 and in Fournié-Zaluski et al., *J. Med. Chem.,* 35, 2473, 1992. However, these compounds do not satisfy the concept of mixed inhibitors, on account of their structure in which an APN inhibitor and an NEP inhibitor are associated by means of a disulphide bridge. These compounds are then reduced by cerebral reductases and each act on their specific target.

According to patent application WO 95/35302 and *Bioorganic & Medicinal Chemistry Letters,* Vol. 6, No. 11, pp 1257–1260, 1996, certain phosphinic acid derivatives are known which have, respectively, an inhibitory activity on endothelin conversion enzyme (ECE) and a mixed inhibitory activity on angiotensin conversion enzyme (ACE) and on neutral endopeptidase (NEP). These compounds are useful in the treatment of cardiovascular diseases.

One of the objects of the invention is to provide novel compounds which behave as true mixed inhibitors of APN and of NEP, and which are capable of jointly inhibiting the two enzymatic activities responsible for the degradation of enkephalins and of manifesting their pharmacological properties after intravenous, cutaneous or oral injection.

These compounds have certain properties of morphinic substances, in particular analgesia, beneficial effects on behaviour (antidepressants, sedatives, anxiolytic agents, inhibition removers and promnesic agents), and peripheral effects (antidiarrhoeic, antitussive, hypotensive, antiinflammatory, etc. effects). Furthermore, one advantage of these compounds is that they have none of the harmful effects of morphinic agents (tolerance, physical and psychic dependency, respiratory depression, intestinal stasis, etc.).

The present invention therefore provides an (α-aminophosphino)peptide of general formula (I)

$$R_1-N(R_2)-CH(R_3)-P(=O)(OR_4)-CH(R_5)-CH(R_6)-CONH-CH(R_7)-(\phantom{)}_n-COOR_8 \quad (I)$$

in which $R_1$ and $R_2$ each represent a hydrogen atom or alternatively $R_1$ and $R_2$, taken together, form an unsaturated group of formula R' (R")C=, in which, R' represents a phenyl group monosubstituted in position 2 with a hydroxyl group, or alternatively a phenyl group disubstituted, in position 2, with a hydroxyl group and, in position 4 or 5, either with a halogen atom or with a nitro group, or with a hydroxyl group, or with an alkoxy group —$OR_9$, R" represents a phenyl group, a phenyl group substituted by 1 to 5 halogen atoms or a heterocyclic aromatic group, hereinafter, the terms $R_9$ and $R_{10}$, used for the definition of radicals, each represent an alkyl group of 1 to 6 carbon atoms, $R_3$ represents a hydrogen atom, an alkyl group or an alkenyl group of 1 to 6 carbon atoms, it being possible for these last two groups to be substituted with:

a hydroxyl group or an alkoxy group —$OR_9$, a phenyl group or a benzyl group, aサulphanyl group, an alkylsulphanyl group —$SR_9$ or an alkylsulphanyl group oxidized on the sulphur atom —$S(O)R_9$, an amino group, a group —$NHR_9$ or —$NR_9R_{10}$, optionally oxidized on the nitrogen atom, or a guanidino group $H_2N-C(=NH)-NH-$, a cycloalkyl or cycloalkylmethyl group, a phenyl group, a benzyl group, which can be substituted on the phenyl group with 1 or 2 of the following substituents:

a halogen atom, a hydroxyl group, an alkoxy group —$OR_9$, an alkylsulphanyl group —$SR_9$ or an alkylsulphanyl group oxidized on the sulphur atom, an amino group or a group —$NHR_9$ or —$NR_9R_{10}$ optionally oxidized on the nitrogen atom, a nitro group, a phenyl group, an alkyl group of 1 to 4 carbon atoms, a methyl group substituted with a heterocyclic aromatic or saturated group, it being possible for the hetero atoms to be oxidized in the form of N-oxide or S-oxide, $R_4$ represents a hydrogen atom, an alkyl or alkenyl group of 1 to 6 carbon atoms, a cycloalkyl group, a cycloalkylalkyl group, a phenyl group, a benzyl group, which can be substituted on the phenyl group with 1 or 2 of the following substituents:

an alkyl group of 1 to 6 carbon atoms, a halogen atom, a hydroxyl group or an alkoxy group —$OR_9$, a trifluoromethyl group, a nitro group, $R_5$ represents
  a hydrogen atom,
  an alkyl group or an alkenyl group of 1 to 6 carbon atoms, it being possible for these last two groups to be substituted with:
    a hydroxyl group or an alkoxy group $—OR_9$,
    a phenyl group or a benzyl group,
    a sulphanyl group, an alkylsulphanyl group $—SR_9$ or an alkylsulphanyl group oxidized on the sulphur atom $—S(O)R_9$,
    an amino group, a group $—NHR_9$ or $—NR_9R_{10}$, optionally oxidized on the nitrogen atom, or
    a guanidino group $H_2N—C(=NH)—NH—$,
  a cycloalkyl or cycloalkylmethyl group,
  a phenyl group, a benzyl group, which can be substituted on the phenyl group with 1 or 2 of the following substituents:
    a halogen atom,
    a hydroxyl group, an alkoxy group $—OR_9$,
    an alkylsulphanyl group $—SR_9$ or an alkylsulphanyl group oxidized on the sulphur atom,
    an amino group or a group $—NHR_9$ or $—NR_9R_{10}$ optionally oxidized on the nitrogen atom,
    a nitro group,
    a phenyl group,
    an alkyl group of 1 to 4 carbon atoms,
    a methyl group substituted with a heterocyclic group, it being possible for the hetero atoms to be oxidized in the form of N-oxide or S-oxide,
$R_6$ and $R_7$ represent, independently of each other,
  a hydrogen atom,
  an alkyl or alkenyl group of 1 to 6 carbon atoms, which can be substituted with:
    a hydroxyl group or an alkoxy group $—OR_9$,
    a sulphanyl group, an alkylsulphanyl group $—SR_9$ or an alkylsulphanyl group oxidized on the sulphur atom $—S(O)R_9$,
    an amino group or an alkylamino group $—NHR_9$,
    a guanidino group $H_2N—C(=NH)—NH—$, or
    a carboxyl group or an alkyloxycarbonyl group $—COOR_9$,
  a phenyl group, a benzyl group, which can be substituted on the phenyl group by 1 or 2 of the following substituents:
    a halogen atom,
    a phenyl group,
    a hydroxyl group or an alkoxy group $—OR_9$,
    an alkylsulphanyl group $—SR_9$ or an alkylsulphanyl group oxidized on the sulphur atom $—S(O)R_9$,
$R_6$ and $R_7$ together represent a saturated or unsaturated 5- or 6-membered ring comprising 1 or 2 hetero atoms, taken from among oxygen, sulphur and nitrogen,
$R_8$ represents,
  a hydrogen atom,
  an alkyl or alkenyl group of 1 to 6 carbon atoms,
  a phenyl group, a benzyl group,
  n is equal to 0 or 1,
with the exception of methyl N-[2-[[(aminomethyl)(methoxy)phosphinyl]methyl]-4-methyl-1-oxopentyl]-(1,1'-biphenyl-4-yl)-L-alaninate hydrochloride.

In the context of the invention the terms below have the following meanings:
  an alkyl group is a linear or branched, saturated hydrocarbon chain,
  an alkenyl group is a linear or branched hydrocarbon chain containing unsaturation,
  a cycloalkyl group is a cyclic hydrocarbon chain comprising 3 to 7 carbon atoms,
  a cycloalkylalkyl group is a cycloalkyl group linked to an alkyl group, this alkyl group comprising 1 to 6 carbon atoms,
  a cycloalkylmethyl group is a cycloalkyl group linked to a methyl group,
  a heterocyclic group is a cyclic, aromatic or non-aromatic, 5- or 6-membered hydrocarbon chain comprising 1 or 2 hetero atoms chosen from oxygen, sulphur and nitrogen atoms.

In the context of the invention, the halogen atoms are preferably chlorine and fluorine.

When a phenyl group is substituted with a phenyl group, this preferably takes place in position 4 in order to form a biphenyl group (which is also written: [1,1'-biphenyl]).

The subject of the present invention is also the addition salts with pharmacologically acceptable acids of the compounds of formula (I) for which $R_1$ and $R_2$ are hydrogen atoms.

A preferred category of compounds according to the invention are those for which the radicals of formula (I) have the following meanings:
  $R_1$, $R_2$, $R_4$ and $R_8$ represent hydrogen atoms,
  n is equal to 0,
  $R_3$ represents
    an alkyl group of 1 to 6 carbon atoms, which can be substituted with an alkoxy group $—OR_9$, a sulphanyl group or an alkylsulphanyl group $—SR_9$,
    a phenyl group, a benzyl group, which can be substituted on the phenyl group with a halogen atom, an alkyl group of 1 to 4 carbon atoms, an alkoxy group $—OR_9$ or an alkylsulphanyl group $—SR_9$,
  $R_5$ represents
    an alkyl group of 1 to 6 carbon atoms, which can be substituted with an alkoxy group $—OR_9$, a sulphanyl group or an alkylsulphanyl group $—SR_9$,
    a phenyl group, a benzyl group, which can be substituted on the phenyl group with a halogen atom, an alkyl group of 1 to 4 carbon atoms, an alkoxy group $—OR_9$ or an alkylsulphanyl group $—SR_9$,
    a biphenylmethyl group,
  $R_6$ represents
    an alkyl group of 1 to 6 carbon atoms, which can be substituted with an alkoxy group $—OR_9$, a sulphanyl group or an alkylsulphanyl group $—SR_9$,
    a phenyl group, a benzyl group, which can be substituted on the phenyl group with a halogen atom, an alkyl group of 1 to 4 carbon atoms, an alkoxy group $—OR_9$ or an alkylsulphanyl group $—SR_9$,
    a biphenylmethyl group.

The compounds of formula (I) can have from 1 to 5 chiral atoms. The compounds of the invention can exist in different isomeric forms, including the form of enantiomers and diastereoisomers. The present invention includes these different forms as well as mixtures thereof, including racemic mixtures.

The carbon bearing the radical $R_6$, when $R_6$ is other than a hydrogen atom, is advantageously of (S) absolute configuration.

The compounds of the invention of formula (I) can be prepared according to the processes described in Appendices 1, 2 and 3.

In the description of the process, the radicals $A_1$, $A_2$ and $A_3$ have the following meanings:
  $A_1$ represents a biphenylmethyl group, a tert-butoxycarbonyl group, a benzyloxycarbonyl group or a fluorenylmethoxycarbonyl group, $A_2$ represents a hydrogen atom, an alkyl group such as methyl or ethyl, or a benzyl group, $A_3$ represents a methyl, ethyl, tert-butyl or benzyl group.

The compounds of formula (Ia), (Ib) and (Ic), which are compounds of formula (I) according to the invention, are prepared according to the process represented in Appendix 1. $R_3$, $R_4$, $R_5$, $R_6$, $R_7$, R' and R" have the meanings given in formula (I). According to this process, a hydroxyphosphinylpropanoic acid derivative of formula (IVb) is reacted with an amino acid derivative of formula (III), in the presence of benzotriazol-1-yloxy-tris(dimethylamino) phosphonium hexafluorophosphate (BOP), in an organic solvent such as dimethylformamide. The compound of formula (III) may be used in the form of a salt, such as the p-toluenesulphonic acid salt. It is then particularly advantageous to work in the presence of a base such as a tertiary amine, for instance diisopropylethylamine. This reaction makes it possible to obtain a compound of formula (IIa).

In the case where $R_5$ represents, in the final product of formula (I), a biphenylmethyl group, the process is performed according to a variant during this step, which consists in carrying out the coupling described above under the same operating conditions, starting with the compound of formula (IVb) and the compound of formula (III), in which the radical $R_5$ firstly represents a (4-bromophenyl)methyl group. The compound of formula (IIa) thus obtained is then reacted with phenylboronic acid in a solvent such as a toluene/methanol mixture and in the presence of tetrakis (triphenylphosphine)palladium and sodium carbonate, in order to obtain the compound of formula (IIa), in which $R_5$ is a biphenylmethyl group.

The compound of formula (IIa) is used to prepare the compound of formula (Ia), in which the three amine, phosphinate and carboxylate functions are deprotected simultaneously or successively. The carboxyl function can be deprotected in order to give a compound of formula (IIb), for example by saponification. The phosphinate function can be deprotected in order to give a compound of formula (IIc). The amine function can be deprotected in order to give a compound of formula (Ia), for example by catalytic hydrogenation or acidic hydrolysis. This is the alternative C, represented in Appendix 1.

According to an alternative mode of preparation, the compound of formula (Ia) can be obtained directly from the compound of formula (IIa) by catalytic hydrogenation, in particular when $A_1$ represents a benzyloxycarbonyl group, $A_2$ represents a benzyl group and $A_3$ represents a benzyl group. This is the alternative B, represented in Appendix 1.

In order to prepare the compound of formula (Ib), in which $R_4$ and $R_8$ are other than a hydrogen atom, the compound of formula (IIc) in which the amine function is protected, is esterified according to methods known to those skilled in the art, which amounts to introducing the radicals $R_4$ and $R_8$, respectively, on the phosphinate function and on the carboxylate function. An alcohol $R_4OH$, in which $R_4$ has one of the meanings given in formula (I) except for hydrogen, can thus be condensed on a compound of formula (IIc), in the presence of a coupling agent such as dicyclohexylcarbodiimide (DCC) and a base such as dimethylaminopyridine (DMAP), on this compound of formula (IIc). Lastly, the amine function is deprotected.

According to an alternative mode of preparation of the compound of formula (Ib), in which the radicals $R_4$ and $R_8$ each represent one of the possible substituents of $A_2$, respectively, with the exclusion of a hydrogen atom, and of $A_3$, the compound of formula (Ib) can be obtained directly by deprotecting only the amine function of the compound of formula (IIa). This is the alternative A, represented in Appendix 1.

In order to prepare the compound of formula (Ic), a ketone R'(R")C=O is condensed with a compound of formula (Ib) if $R_4$ and $R_8$ are other than a hydrogen atom, and with a compound of formula (Ia) if $R_4$ and $R_8$ represent a hydrogen atom, these ketones R'(R")C=O being obtained by Fries rearrangement of the corresponding esters R'CO$_2$R'.

The compounds of formula (III), in which n can be equal to 0 or 1, $R_6$ and $R_7$ taking one of the meanings given in formula (I), represent a natural or non-natural α- or β-amino acid. They can be synthesized according to the standard methods that are well known to those skilled in the art.

The compounds of formula (IVb) can be prepared according to the processes described in Appendices 2 and 3. The compound of formula (IVb) is obtained from the compound of formula (IVa) by a standard saponification.

The final step of the process is represented in Scheme 1 of Appendix 2. According to this final step of the process, a phosphonic acid derivative of formula (VIb) is added to an acrylic ester derivative of formula (V), in the presence of N,O-bis(trimethylsilyl)acetamide, without solvent or in an inert organic solvent such as acetonitrile.

The compound of formula (VIb) is obtained by indirect or direct synthesis, represented in Scheme 2 of Appendix 2:

via the indirect route, the process consists in treating diphenylmethylamine with phosphonous acid and in reacting the diphenylmethylamine, in the form of the phosphonous acid salt obtained, with an aldehyde $R_3CHO$ in anhydrous ethanol in order to obtain a compound of formula (X). The amine function of this compound of formula (X) is then deprotected in water, optionally acidified with an inorganic acid, such as hydrochloric acid or hydrobromic acid, and the compound obtained is then treated with propylene oxide in order to lead to the compounds of formula (VII), which are finally acylated in order to obtain a compound of formula (VIa), via the direct route, the process consists in treating diphenylmethylamine hydrochloride with phosphonous acid and an aldehyde $R_3CHO$, this reaction being carried out in a mixture of ethanol and water at reflux.

The compounds of formula (V) can be obtained by two methods, which are represented in Appendix 3, respectively in Schemes 3 and 4:

according to the first process (Scheme 3), a halide, and preferably a bromide, of alkyl or of aralkyl $R_5X$ is reacted with triethyl phosphonoacetate in the presence of sodium hydride in order to obtain a compound of formula (VIII), which is reacted with formaldehyde, in the presence of potassium carbonate, in order to obtain a compound of formula (V), according to the second process (Scheme 4), the compounds of formula (V) are obtained by a Mannich reaction on a monoester of a malonic acid of formula (IX).

Another aspect of the invention relates to the compounds of formula (IIa), which are useful in particular as synthetic intermediates for the preparation of the compounds of formula (I). They can also be in the form of isomers, including the form of enantiomers and diastereoisomers and mixtures of these different forms, as well as in the form of addition salts.

However, the following compounds, described in B. P. Morgan et al., "differential binding energy: a detailed evaluation of the influence of hydrogen-bonding and hydrophobic groups on the inhibition of thermolysin by phosphorus-containing inhibitors, *Journal of the American Chemical Society* (1991), 113, 297–307, are excluded:

methyl N-[2-[[methoxy[[[(phenylmethoxy)carbonyl)
  amino]-methyl]phosphinyl]methyl]-4-methyl-1-
  oxopentanyl]-L-alaninate,
methyl N-[-[[methoxy[[[(phenylmethoxy)carbonyl]amino]
  methyl]phosphinyl]methyl]-4-methyl-1-oxopentanyl]-L-
  glycinate,
methyl N-[-[[methoxy[[[(phenylmethoxy)carbonyl]amino]
  methyl]phosphinyl]methyl]-4-methyl-1-oxopentanyl]-L-
  phenylalaniante and,
methyl N-[-[[methoxy[[[(phenylmethoxy)carbonyl]amino]
  methyl]phosphinyl]methyl]-4-methyl-1-oxopentanyl]-L-
  leucinate.

The compounds of general formula (I) thus obtained are in the form of isomers, including the form of enantiomers, diastereoisomers and mixtures of these different forms, including racemic mixtures. The compounds of formula (I), which are optically pure, are obtained by semi-preparative HPLC separation (Chromasil $C_8$, 10 mm, 20×250 mm, acetonitrile/water, 15 ml/min).

They can also be obtained by resolution, starting with a chiral amine of the phosphinic acid derivative of formula (VIb), in which $A_2$=H, followed by diastereoselective Michael addition, in the presence of chiral inducers, which leads to the compounds of formula (IV), which are of fully defined stereochemistry.

The examples which follow are intended to illustrate the preparation of a number of compounds of the invention. The elemental analyses and the NMR spectra confirm the structures of the compounds obtained.

In the compound names, the hyphen "-" forms part of the name, and the line "_" serves merely to indicate the end-of-line break; it should be removed if it is not at the end of a line and it should not be replaced either by a normal hyphen or by a space.

In the examples which follow, the racemic mixture obtained for each of the compounds can be separated on a Chromasil $C_8$ preparative column (10 mm, 20×250 mm, 15 ml/min) with an acetonitrile/water mixture. The amino acids used in these syntheses have an (S) absolute configuration and a mixture of four diastereoisomers is thus obtained. By convention, these diastereoisomers are referred to as A, B, C and D in order of increasing retention time. The retention times of the compounds are collated in the table.

EXAMPLE 1

N-[2-[[(1-Amino-2-phenylethyl)hydroxyphosphinyl]
methyl]-1-oxo-3-phenylpropyl]-L-phenylalanine
Hydrochloride 1.1. α-Phenylbenzenemethanamine phosphinate To a solution of 8 g (121.2 mmol) of phosphonous acid in 30 ml of anhydrous ethanol, cooled to 0° C., are added dropwise 22.21 g (121.2 mmol) of diphenylmethylamine, while taking care to ensure that the temperature does not exceed 25° C. After addition, a white precipitate forms, to which 200 ml of diethyl ether are added. The precipitate is filtered off, rinsed with diethyl ether and then dried. 22.66 g of product are recovered (yield=98.2%).

Melting point: 176–177° C.

1.2. [1-[(Diphenylmethyl)amino]-2-phenylethyl)phosphinic acid

A solution of 21 g (84.3 mmol) of α-phenylbenzenemethanamine phosphinate in 60 ml of anhydrous ethanol is brought to reflux. 20.25 g (168.5 mmol) of phenylacetaldehyde in 20 ml of anhydrous ethanol are added dropwise. An abundant white precipitate forms. After addition, refluxing is continued for 2.5 hours. After cooling, 100 ml of acetone are added. The precipitate obtained is filtered off and washed with the same solvent. 18.6 g of product are recovered (yield=62.9%).

Melting point: 211° C.

1.3. (1-Amino-2-phenylethyl)phosphinic acid

A mixture of 14.6 g (41.6 mmol) of [1-[(diphenylmethyl)amino]-2-phenylethyl]phosphinic acid and 94 ml of aqueous 48% hydrobromic acid is refluxed for 2 hours. Two phases appear. The mixture is brought to dryness by evaporation under vacuum and under warm conditions and is then taken up in 94 ml of water. The aqueous phase is washed three times with diethyl ether. The aqueous phase, again evaporated, gives (1-amino-2-phenylethyl)phosphinic acid hydrobromide, which is taken up in 58 ml of absolute ethanol. 20.4 ml of propylene oxide are added dropwise, with stirring, at 0° C. The formation of an abundant white precipitate is observed, which is filtered off and washed with diethyl ether. 6.77 g of product are recovered (yield=87.9%).

Melting point: 226–227° C.

1.4. [2-Phenyl-1-[[(phenylmethoxy)carbonyl]amino]ethyl] phosphinic acid

To a solution of 7 g (37.8 mmol) of (1-amino-2-phenylethyl)phosphinic acid in 86 ml of a mixture of dioxane and water, in the presence of one equivalent of sodium hydroxide (1.51 g), are added dropwise, at 0° C and simultaneously, a solution of 7.55 g (44.26 mmol) of benzyl chloroformate in 21 ml of dioxane and, in order to keep the pH of the reaction at about 9, a solution of 2.42 g of sodium hydroxide in 21 ml of water. At the end of the addition, the mixture is maintained at a temperature in the region of 20° C. for 2 hours. The aqueous phase is then washed with 3 times 20 ml of diethyl ether. The aqueous phase is acidified, at 0° C., with vigorous stirring, using 27 ml of 6N hydrochloric acid solution. The abundant white precipitate formed is filtered off, washed with water and dried. 12.08 g of product are recovered (yield=83.7%).

Melting point: 135–136° C.

1.5. Methyl α-methylenebenzenepropanoate

To a solution of 20 g (123.5 mmol) of α-methylenebenzenepropenoic acid in 12 ml of methanol, cooled to 0° C., are added dropwise 2.7 ml of thionyl chloride. The mixture is maintained at reflux for 6 hours and the solvent is then evaporated off under reduced pressure. The residue is taken up in 30 ml of ethyl acetate. This solution is washed with 10% sodium hydrogen carbonate and then with water. The organic phase is dried over sodium sulphate, filtered and evaporated under reduced pressure. The residue is purified by chromatography on silica gel, eluting with a 1/3 ethyl acetate/hexane mixture. 21.3 g of product are recovered in the form of an oil (yield=98%).

1.6. Methyl 3-[hydroxy[2-phenyl-1-[[(phenylmethoxy) carbonyl]amino]ethyl]phosphinyl]-2-(phenylmethyl) propanoate A solution of 1 g (3.31 mmol) of [2-phenyl-1-[[(phenylmethoxy)carbonyl]amino]ethyl]phosphinic acid, 0.66 g (3.75 mmol) of methyl α-methylenebenzenepropanoate and 3.1 ml of N,O-bis(trimethylsilyl)acetamide is maintained at 60° C. for 24 hours. After cooling, 60 ml of a 1/1 ethyl acetate/water mixture are added. The aqueous phase is extracted with ethyl acetate. The combined organic phases are washed with water, dried over sodium sulphate, filtered and evaporated under vacuum. The residue is purified by recrystallization from a mixture of ethyl acetate and hexane. 1.04 g of product are recovered (yield=67%).

Melting point: 161–163° C.

1.7. 3-[Hydroxy[2-phenyl-1-[[(phenylmethoxy)carbonyl] amino]ethyl]phosphinyl]-2-(phenylmethyl)propanoic acid To a solution of 1 g (2.02 mmol) of methyl 3-[hydroxy[2-phenyl-1-[[(phenylmethoxy)carbonyl)amino]ethyl]

phosphinyl]-2-(phenylmethyl)propanoate in 20 ml of methanol are added 20 ml of 1N sodium hydroxide. After stirring for 10 hours, the medium is acidified with 2N hydrochloric acid, the methanol is then evaporated off and the residue is extracted three times with ethyl acetate. The combined organic phases are washed with water, dried over sodium sulphate and evaporated. 0.97 g of product is recovered (yield=100%).

Melting point: 178–179° C.

1.8. Phenylmethyl N-[2-[[hydroxy[2-phenyl-1-[[(phenylmethoxy)carbonyl]amino]ethyl]phosphinyl]methyl]-1-oxo-3-phenylpropyl]-L-phenylalaninate To 200 mg (0.42 mmol) of 3-[hydroxy[2-phenyl-1-[[(phenylmethoxy)carbonyl]amino]ethyl]phosphinyl]-2-(phenylmethyl)propanoic acid, 178 mg (0.42 mmol) of phenylmethyl L-phenylalaninate in the form of the p-toluenesulphonic acid salt and 384 mg (0.87 mmol) of BOP in 0.8 ml of dimethylformamide is added, with stirring at a temperature in the region of 20° C., 0.7 ml of diisopropylethylamine. After reaction for 30 minutes at this temperature, the dimethylformamide is evaporated off under reduced pressure and 12 ml of 1N hydrochloric acid are added to the oily residue obtained. The precipitate is filtered off, washed with water and dried. 210 mg of product are recovered (yield=70.3%).

Melting point: 173–176° C.

1.9. N-[2-[[(1-Amino-2-phenylethyl)hydroxyphosphinyl]methyl]-1-oxo-2-phenylpropyl]-L-phenylalanine hydrochloride To a solution of 140 mg (0.19 mmol) of phenylmethyl N-[2-[[hydroxy[2-phenyl-1-[[1-(phenylmethoxy)carbonyl]amino]ethyl]phosphinyl]methyl]-1-oxo-3-phenylpropyl]-L-phenylalaninate in 20 ml of methanol are added, at 0° C., 20 mg of palladium-on-charcoal. The mixture is then hydrogenolysed at a temperature in the region of 20° C., with stirring, in the presence of a stream of hydrogen. After 2 hours, the reaction mixture is filtered and the filter cake is rinsed with methanol. One equivalent of 6N hydrochloric acid is added to the filtrate. The solution is evaporated under reduced pressure. 87 mg of product are recovered (yield=84.1%).

Melting point: 220° C. (decomposition).

EXAMPLE 2

N-[2-[[(1-Amino-2-phenylethyl)hydroxyphosphinyl]methyl]-1-oxo-3-phenylpropyl]-L-alanine Hydrobromide 2.1. Phenylmethyl N-[2-[[hydroxy[2-phenyl-1-[[(phenylmethoxy)carbonyl]amino]ethyl]phosphinyl]methyl]-1-oxo-3-phenylpropyl]-L-alaninate The process is performed according to the operating conditions described in 1.8, starting with 300 mg (0.62 mmol) of 3-[hydroxy[2-phenyl-1-[[(phenylmethoxy)carbonyl]amino]ethyl]phosphinyl]-2-(phenylmethyl) propanoic acid synthesized in 1.7., and 219 mg (0.62 mmol) of phenylmethyl alaninate in the form of the p-toluenesulphonic acid salt. 288 mg of product are recovered (yield=71.9%).

Melting point: 171–174° C.

2.2. N-[2-[[Hydroxy[2-phenyl-1-[[(phenylmethoxy)carbonyl]amino]ethyl]phosphinyl]methyl]-1-oxo-3-phenylpropyl]-L-alanine The process is performed according to the operating conditions described in 1.7., starting with 100 mg (0.16 mmol) of phenylmethyl N-[2-[[hydroxy[2-phenyl1-1-[[(phenylmethoxy)carbonyl]amino]ethyl]phosphinyl] methyl]-1-oxo-3-phenylpropyl]-L-alaninate 83.7 mg of product are recovered (yield=97.4%)

Melting point: 192–195° C.

2.3. N-[2-[[(1-Amino-2-phenylethyl)hydroxyphosphinyl]methyl]-1-oxo-3-phenylpropyl]-L-alanine hydrobromide To a solution of 50 mg (0.09 mmol) of N-[2-[[hydroxy [2-phenyl-1-[[(phenylmethoxy)carbonyl]amino]ethyl] phosphinyl]methyl]-1-oxo-3-phenylpropyl]-L-alanine in 2.5 ml of dichloromethane, cooled to −10° C., is added, under nitrogen, 0.45 ml of boron tribromide as a 1M solution in dichloromethane (0.45 mmol). The mixture is stirred for one hour at −10° C. and then for two hours at a temperature in the region of 20° C. 3 ml of water are added and the dichloromethane is evaporated off. The aqueous phase is washed with diethyl ether and evaporated to dryness. The product is taken up in water and then freeze-dried. 45 mg of product are recovered (yield=100%).

Melting point: 210° C. (decomposition).

The Following Are Obtained in a Similar Manner

Compounds Nos. 3, 4 and 5, starting with suitable starting materials. The α-amino acid carboxylates used are obtained either from natural amino acids or are synthesized according to methods known to those skilled in the art.

EXAMPLE 3

(S)-β-[[3-[(1-Amino-2-phenyl-ethyl)hydroxyphosphinyl]-1-oxo-2-(phenylmethyl)propyl] amino]benzenebutanoic Acid Hydrobromide 3.1. 1,1-Dimethylethyl (S)-[3-diazo-2-oxo-1-phenylmethyl) propyl]carbamate To a solution of 10 g (37.69 mmol) of N-[(1,1-dimethylethoxy)carbonyl]-L-phenylalanine in 56 ml of anhydrous tetrahydrofuran cooled to a temperature of −20° C. are added, under argon, 3.7 ml of N-methylmorpholine, followed by dropwise addition of 4.4 ml of isobutyl chloroformate over 30 minutes and the mixture is then filtered. The excess methanediazonium dissolved in diethyl ether is added to the filtrate. The mixture is stirred, under argon, for 30 minutes at −20° C. and then for 2 hours at a temperature in the region of 20° C. The excess methanediazonium is removed by flushing with argon. The solvent is evaporated off under reduced pressure. The residue is taken up in ethyl acetate, washed successively with water, with 10% citric acid, with 1N sodium hydrogen carbonate and with water, dried over sodium sulphate and filtered. The solvent is evaporated off under reduced pressure. 10.7 g of product are recovered (yield=98%).

Melting point: 95–96° C.

3.2. Methyl (S)-β-[[(1,1-dimethyl-ethoxy)carbonyl]amino] benzenebutanoate

To a solution of 10.7 g (36.98 mmol) of 1,1-dimethylethyl (S)-[3-diazo-2-oxo-1-(phenylmethyl)propyl]carbamate in 110 ml of methanol are added, under nitrogen, 12 ml of silver benzoate solution (1.15 g in 23 ml of triethylamine). The mixture is stirred at a temperature in the region of 20° C. for 30 minutes. A further 5.5 ml of silver benzoate is the same solvent are added. The mixture is stirred for a further 2 hours. 35 ml of saturated sodium chloride, Celite and activated charcoal are added. After filtration, the solvent is evaporated off under reduced pressure. The resiude is taken up in ethyl acetate, washed successively with water, with 1N sodium hydrogen carbonate, with 1N hydrochloric acid and with water, dried over sodium sulphate and filtered. The solvent is evaporated off under reduced pressure. The prod uct is purified by recrystallization from hexane. 8.4 g of product are recovered (yield=78%).

Melting point: 51–52° C.

3.3. Methyl (S)-β-aminobenzenebutanoate

To a solution of 3 g (10.24 mmol) of methyl (S)-β-[[(1,1-dimethylethoxy)carbonyl]amino]benzenebutanoate in 1.2 ml of dichloromethane are added 1.2 ml of trifluoroacetic acid. The mixture is stirred at a temperature in the region of 20° C. for one hour. The solvent is evaporated to dryness under reduced pressure. The residue is taken up in 40 ml of dichloromethane. 1N sodium hydroxide is added to pH=8. The organic phase is washed with water, dried over sodium sulphate and filtered. The solvent is evaporated off under reduced pressure. 1.89 g of product are recovered (yield=95.6%).

$R_f$ (ethyl acetate) : 0.26

3.4. (S)-β-[3-[[(1-Amino-2-phenylethyl) hydroxyphosphinyl]-1-oxo-2-(phenylmethyl)propyl] amino]benzenebutanoic acid hydrobromide The process is performed according to the operating conditions described in 1.8., starting with 3-[hydroxy[2-phenyl-1-[[(phenylmethoxy)carbonyl]amino]ethyl] phosphinyl]-2-(phenylmethyl)propanoic acid and methyl (S)-β-aminobenzenebutanoate (yield=71.3%), after which the process is performed successively, using, as starting material in each case, the compound synthesized in the previous step, according to the operating conditions described in 1.7. (yield=94%), and then in 2.3. (yield=100%).

Melting point: 240° C. (decomposition).

EXAMPLE 4

N-[2-[[(1-Amino-2-phenylethyl)hydroxyphosphinyl] methyl]-4-methyl-1-oxopentyl)-L-phenylalanine hydrobromide 4.1. Ethyl 2-(diethoxyphosphinyl)-4-methylpentanoate To a solution of 31 ml (156 mmol) of ethyl (diethylphosphinyl)acetate in 49 ml of dimethylformamide are added, at −10° C., 5.16 g (172 mmol) of 80% sodium hydride. After 15 minutes, 17.6 ml (162 mmol) of isobutyl bromide are added dropwise. The reaction mixture is brought to a temperature in the region of 20° C. and stirred at this temperature overnight. The solvent is evaporated off under reduced pressure. The residue is taken up in ethyl acetate, washed with water, dried over sodium sulphate and filtered. The solvent is evaporated off under reduced pressure. The product is purified by chromatography on silica gel, eluting with a 1/1 ethyl acetate/heptane mixture. 23.7 g of product are recovered in the form of an oil (yield=54.3%).

Rf (3.5/6.5 heptane/ethyl acetate): 0.39.

4.2. Ethyl 4-methyl-2-methylenepentanoate

A mixture of 19 g (67.9 mmol) of ethyl 2-(diethoxyphosphinyl)-4-methylpentanoate, 27 ml (360.3 mmol) of formaldehyde and 28 g (202.6 mmol) of potassium carbonate is maintained at reflux for 3 hours. A mixture of water and diethyl ether is added. The aqueous phase is extracted with diethyl ether. The combined organic phases are washed with water, dried over sodium sulphate, filtered and evaporated under reduced pressure. The residue is distilled under reduced pressure. 6.7 g of product are recovered in the form of an oil (yield=63.3%).

4.3. Ethyl 2-[[hydroxy[2-phenyl-1-[[(phenylmethoxy) carbonyl]amino]ethyl]phosphinyl]methyl]-4-methylpentanoate To a solution of 1 g (3.13 mmol) of [2-phenyl-1-[[(phenylmethoxy)carbonyl]amino]ethyl]phosphinic acid synthesized in 1.4., 2.2 g (14.10 mmol) of ethyl 4-methyl-2-methylenepentanoate and 0.52 ml of N,O-bis (trimethylsilyl)acetamide in 0.27 ml of acetonitrile is stirred at a temperature in the region of 20° C. for 24 hours. 60 ml of a 1/1 ethyl acetate/water mixture are added. The aqueous phase is extracted with ethyl acetate and the combined organic phases are washed with water, dried over sodium sulphate, filtered and evaporated under vacuum. The product is purified by recrystallization from a mixture of ethyl acetate and hexane. 1.21 g of product are recovered (yield=81.3%).

Melting point: 143–144° C.

4.4. 2-[[Hydroxy[2-phenyl-1-[[(phenylmethoxy)carbonyl] amino]ethyl]phosphinyl]methyl]-4-methylpentanoic acid The process is performed according to the operating conditions described in 1.7., starting with 510 mg (1.07 mmol) of ethyl 2-[[hydroxy[2-phenyl-1-[[(phenylmethoxy) carbonyl]amino]ethyl]phosphinyl]methyl]-4-methylpentanoate. 479 mg of product are recovered (yield=99.8%).

Melting point: 170–172° C.

4.5. Methyl N-[2-[[hydroxy[2-phenyl-1-[[(phenylmethoxy) carbonyl]amino]ethyl]phosphinyl]methyl]-4-methyl-1-oxopentyl]-L-phenylalaninate The process is performed according to the procedure described in 1.8., starting with 250 mg (0.58 mol) of 2-[[hydroxy[2-phenyl-1-[[(phenylmethoxy)carbonyl] amino]ethyl]phosphinyl]methyl]-4-methylpentanoic acid and 124.5 mg (0.58 mmol) of methyl phenylalaninate hydrochloride. 228 mg of product are recovered (yield=65%).

Melting point: 150–152° C.

4.6. N-[2-[[Hydroxy[2-phenyl-1-[[(phenylmethoxy) carbonyl]amino]ethyl]phosphinyl]methyl]-4-methyl-1-oxopentyl]-L-phenylalanine The process is performed according to the procedure described in 1.7., starting with 180 mg (0.30 mmol) of methyl N-[2-[[phydroxy[2-phenyl-1-[[(phenylmethoxy) carbonyl]amino]ethyl]phosphinyl]methyl]-4-methyl-1-oxopentyl)-L-phenylalaninate. 158 mg of product are recovered (yield=89.9%).

Melting point: 171–173° C.

4.7. N-[2-[[(1-Amino-2-phenylethyl)hydroxyphosphinyl] methyl]-4-methyl-1-oxopentyl]-L-phenylalanine hydrobromide The process is performed according to the procedure described in 2.3., starting with 120 mg (0.20 mmol) of N-[2-[[hydroxy[2-phenyl-1-[[(phenylmethoxy)carbonyl] amino]ethyl]phosphinyl]methyl]-4-methyl-1-oxopentyl]-L-phenylalanine. 109 mg of product are recovered (yield=100%).

Melting point: 230° C. (decomposition).

EXAMPLE 5

N-[3-[(1-Amino-2-phenylethyl)hydroxyphosphinyl]-2-([1,1'-bisphenyl]-4-ylmethyl)-1-oxopropyl]-L-alanine Hydrobromide 5.1. Ethyl 4-bromo-α-(diethoxyphosphinyl) benzenepropanoate Starting with 9 ml (45.36 mmol) of triethyl phosphonoacetate and 11.8 g (47.34 mmol) of (4-bromophenyl)methyl bromide, the process is performed according to the operating conditions described in 4.1. 7.8 g of product are recovered in the form of an oil (yield=43.73%).

Rf (1/4 heptane/ethyl acetate): 0.46.

5.2. Ethyl 4-bromo-α-methylenebenzenepropanoate

Starting with 5.5 g (14 mmol) of ethyl 4-bromo-α-(diethoxyphosphinyl)benzenepropanoate and 5.3 ml (71 mmol) of formaldehyde, the process is performed according to the operating conditions described in 4.2. The product is purified by chromatography on silica gel, eluting with a 1/20 ethyl acetate/heptane mixture. 2.82 g of product are recovered in the form of an oil (yield=75%).

Rf (9/1 heptane/ethyl acetate): 0.57.

5.3. Ethyl 3-(4-bromophenyl)-2-[[hydroxy[2-phenyl-1-[[(phenylmethoxy)carbonyl]amino]ethyl]phosphinyl]methyl]propanoate The process is performed according to the operating conditions described in 1.6., starting with 2 g (6.27 mmol) of [2-phenyl-1-[(phenylmethoxy)carbonyl]aminoethyl]phosphinic acid synthesized in 1.4. and 2 g (7.44 mol) of ethyl 4-bromo-α-methylenebenzenepropanoate. 3.1 g of product are recovered (yield=84.1%)

Melting point: 124–125° C.

5.4. Ethyl 3-[1,1'-biphenyl]-4-yl-2-[[hydroxy[2-phenyl-1-[[(phenylmethoxy)carbonyl]amino]ethyl]phosphinyl]methyl]propanoate 200 mg (0.34 mmol) of ethyl 3-(4-bromophenyl)-2-[[hydroxy[2-phenyl-1-[[(phenyl-methoxy)carbonyl]amino]ethyl]phosphinyl]methyl]propanoate are condensed with 42 mg (0.34 mmol) of phenylboronic acid, working in 1.8 ml of a 2/1 toluene/methanol mixture, tetrakis(triphenylphosphine)palladium and 0.4 ml of 2M sodium carbonate (0.8 mmol). The reaction mixture is stirred for 6 hours under nitrogen and at reflux. After cooling, 10 ml of ethyl acetate are added and the mixture is acidified to pH=3 with aqueous 2N hydrochloric acid solution. After filtration through Celite, rinsed with ethyl acetate, the solvent is evaporated off under reduced pressure. The product is purified by recrystallization from a mixture of ethyl acetate and hexane. 180 mg of product are recovered (yield=90.4%).

Melting point: 164–165° C.

5.5. 3-[1,1'-Biphenyl]-4-yl-2-[[hydroxy[2-phenyl-1-[[(phenylmethoxy)carbonyl]amino]ethyl]methyl]phosphinyl]propanoic acid The process is performed according to the operating conditions described in 1.7., starting with 180 mg (0.31 mmol) of ethyl 3-[1,1'-biphenyl]-4-yl-2-[[hydroxy[2-phenyl-1-[[(phenylmethoxy)carbonyl]amino]ethyl]phosphinyl]methyl]propanoate 167 mg of product are recovered (yield=97.4%).

Melting point: 180–182° C.

5.6. Methyl N-[3-[1,1'-biphenyl]-4-yl-2-[[hydroxy[2-phenyl-1-[[(phenylmethoxy)carbonyl]amino]ethyl]phosphinyl]methyl]-1-oxopropyl]-L-alaninate The process is performed according to the operating conditions described in 1.8., starting with 160 mg (0.29 mmol) of 3-[1,1'-biphenyl]-4-yl-2-[[hydroxy [2-phenyl-1-[[(phenylmethoxy)carbonyl]amino]ethyl]methyl]phosphinyl]propanoic acid and 124.5 mg (0.58 mmol) of methyl alaninate hydrochloride. 120 mg of product are recovered (yield=65%).

Melting point: 168–171° C.

5.7. N-[3-[1,1'-Biphenyl]-4-yl-2-[[hydroxy[2-phenyl-1-[[(phenylmethoxy)carbonyl]amino]ethyl]phosphinyl]methyl]-1-oxopropyl]-L-alanine The process is performed according to the operating conditions described in 1.7., starting with 94 mg (0.30 mmol) of methyl N-[3-[1,1'-biphenyl]-4-yl-2-[[hydroxy[2-phenyl-1-[[(phenylmethoxy)carbonyl]amino]ethyl]phosphinyl]methyl]-1-oxopropyl]-L-alaninate. 92 mg of product are recovered (yield=100%).

Melting point: 189–192° C.

5.8. N-[3-[(1-Amino-2-phenylethyl)hydroxyphosphinyl]-2-([1,1'-biphenyl]-4-ylmethyl)-1-oxopropyl]-L-alanine hydrobromide The process is performed according to the operating conditions described in 2.3., starting with 90 mg (0.14 mmol) of N-[3-[1,1'-biphenyl]-4-yl-2-[[hydroxy[2-phenyl-1-[[(phenylmethoxy)carbonyl]amino]ethyl]phosphinyl]methyl]-1-oxopropyl]-L-alanine. 82.4 mg of product are recovered (yield=100%).

Melting point: 210° C. (decomposition).

The Following are Obtained in a Similar Manner Compounds Nos. 22, 23 and 24 in the table.

EXAMPLE 6

N-[2-[[(1-Aminoethyl)hydroxyphosphinyl]methyl]-1-oxo-3-phenylpropyl]-L-phenylalanine Hydrobromide 6.1. [1-[(Diphenylmethyl)amino]ethyl]phosphinic acid A solution of 10 g (45.45 mmol) of diphenylmethylamine hydrochloride and 4.8 ml (46.33 mmol) of hypophosphorus acid at a concentration of 50% in water, in 100 ml of a 90/10 water/ethanol mixture is brought to reflux. 4 g (0.09 mmol) of acetaldehyde are added dropwise. After addition, refluxing is maintained for one hour. The precipitate obtained is filtered and washed with 100 ml of water and 100 ml of acetone. 8 g of product are recovered (yield=64%).

Melting point 236° C.

6.2. (1-Aminoethyl)phosphinic acid

A mixture of 4.5 g (16.36 mmol) of [1-[(diphenylmethyl)amino]ethyl]phosphinic acid and 30 ml of 6N hydrochloric acid is maintained at reflux for 2 hours. Two phases appear. The mixture is brought to dryness by evaporation under vacuum and under warm conditions and is then taken up in 30 ml of water. The aqueous phase is washed three times with diethyl ether. The aqueous phase, again evaporated, gives (1-aminoethyl)phosphinic acid hydrochloride, which is taken up in 15 ml of absolute ethanol. 8 ml of propylene oxide are added dropwise, with stirring, at 0° C. The formation of an abundant white precipitate is observed, which is filtered off and washed with diethyl ether. 1.7 g of product are recovered (yield=95.3%).

Melting point: 222–224° C. (decomposition).

6.3. [1-[[(Phenylmethoxy)carbonyl]amino]ethyl]phosphinic acid

The process is performed according to the operating conditions described in 1.4., starting with 1.7 g (15.6 mmol) of (1-aminoethyl)phosphinic acid and 3.12 g (18.29 mmol) of benzyl chloroformate. 2.8 g of product are recovered (yeld=73.9%).

Melting point: 132–134° C.

6.4. Methyl α-[[hydroxy[1-[[(phenylmethoxy)carbonyl]amino]ethyl]phosphinyl]methyl]benzenepropanoate A solution of 0.6 g (2.47 mmol) of 1-[[(phenylmethoxy)carbonyl]amino]ethyl]phosphinic acid, 2.17 g (12.3 mmol) of methyl 2-(phenylmethyl)propenoate and 0.52 ml of N,O-bis(trimethylsilyl)acetamide in 0.27 ml of acetonitrile is stirred at a temperature in the region of 20° C. for 24 hours. 60 ml of a 1/1 ethyl acetate/water mixture are added. The aqueous phase is extracted with ethyl acetate. The combined organic phases are washed with water, dried over sodium sulphate, filtered and evaporated off under vacuum. The product is purified by recrystallization from a mixture of ethyl acetate and hexane. 0.71 g of product are recovered (yield=68.9%).

Melting point: 154–155° C.

6.5. N-[2-[[(1-Aminoethyl)hydroxyphosphinyl]methyl]-1-oxo-3-phenylpropyl]-L-phenylalanine hydrobromide The process is performed successively, using, in each step, as starting material, the compound synthesized in the previous step, according to the operating conditions described in 1.7. (yield=90.2%), in 1.8. (yield=89.4%), in 1.7. (yield=91%) and then in 2.3. (yield=100%). The α-amino acid carboxylate used is methyl phenylalaninate.

Melting point: 230° C. (decomposition).

EXAMPLE 7

N-[3-[(1-Aminoethyl)hydroxyphosphinyl]-2- ([1,1'-biphenyl ]-4-ylmethyl]) -1-oxopropyl]-L-phenylalanine Hydrobromide 7.1. Ethyl 3-(4-bromophenyl)-2-[[hydroxy[1-[[(phenylmethoxy)carbonyl]amino]ethyl]phosphinyl]methyl]propanoate The process is performed according to the operating conditions described in 5.3., starting with 2.6 g (9.67 mmol) of ethyl 4-bromo-α-methylenebenzenepropanoate and 2 g (8.23 mmol) of [1-[[(phenylmethoxy)carbonyl]amino]ethyl]phosphinic acid. 3.79 g of product are recovered (yield= 90%).

Melting point: 120–122° C.

7.2. Ethyl 3-[1,1'-biphenyl]-4-yl-2-[[hydroxy[1-[[(phenylmethoxy)carbonyl]amino]ethyl]phosphinyl]methyl]propanoate The process is performed according to the operating conditions in 5.4., starting with 1.7 g (3.32 mmol) of ethyl 3-(4-bromophenyl)-2-[[hydroxy[1-[[(phenylmethoxy)carbonyl]amino]ethyl]phosphinyl]methyl]propanoate and 4.05 g (3.32 mmol) of phenylboronic acid. 1.65 g of product are recovered (yield=97.6%).

Melting point: 198° C. (decomposition).

7.3. N-[3-[(1-Aminoethyl)hydroxyphosphinyl]-2-([1,1'-biphenyl]-4-ylmethyl)-1-oxopropyl]-L-phenylalanine hydrobromide The process is performed successively, using, in each step, as starting material, the compound synthesized in the previous step, according to the operating conditions described in 1.7. (yield=88.2%), in 1.8. (yield=65%), in 1.7. (yield=95%) and then in 2.3. (yield=100%).

Melting point: 225° C. (decomposition).

EXAMPLE 8

N-[3-[(1-Aminoethyl)hydroxyphosphinyl]-2-([1,1'-biphenyl]-4-ylmethyl) -1-oxopropyl]-L-alanine Hydrobromide The process is performed according to the operating conditions described in 5.3., starting with ethyl 4-bromo-α-methylenebenzenepropanoate and [1-[[(phenylmethoxy)carbonyl]amino]ethyl]phosphinic acid, in 5.4., starting with the compound obtained, after which the process is performed successively, using, in each step, as starting material, the compound synthesized in the previous step, according to the operating conditions described in 1.7. (yield=88.2%), in 1.8. (yield=83%), in 1.7. (yield=95%) and then in 2.3. (yield=100%).

Melting point: 225° C. (decomposition).

EXAMPLE 9

N-[2-[[(Aminophenylmethyl)hydroxyphosphinyl]methyl]-1-oxo-3-phenylpropyl]-L-phenylalanine Hydrobromide 9.1. [1-(Diphenylmethyl)amino-2-phenylmethyl]phosphinic acid The process is performed according to the operating conditions described in 1.2., starting with 5 g (20 mmol) of α-phenylbenzenemethanamine phosphinate and 4.08 g (40.12 mmol) of benzaldehyde. 2.9 g of product are recovered (yield=43%).

Melting point: 212° C.

9.2. (Aminophenylmethyl)phosphinic acid

The process is performed according to the operating conditions described in 1.3., starting with 22.1 g (65.58 mmol) of [1-(diphenylmethyl)amino-2-phenylmethyl]phosphinic acid. 9.6 g of product are recovered (yield=86%).

Melting point: 243° C.

9.3. [[[(Phenylmethoxy)carbonyl]amino]phenyl-methyl]phosphinic acid

The process is performed according to the operating conditions described in 1.4., starting with 1 g (5.85 mmol) of (aminophenylmethyl)phosphinic acid and 1.17 g (6.86 mmol) of benzyl chloroformate. 1.6 g of product are recovered (yield=90%).

Melting point: 143° C.

9.4. N-[2-[[(Aminophenylmethyl)hydroxyphosphinyl]methyl]-1-oxo-3-phenylpropyl]-L-phenylalanine hydrobromide The process is performed according to the operating conditions described in 1.6., starting with methyl 2-(phenylmethyl)propenoate and [[[(phenylmethoxy)carbonyl]amino]phenylmethyl]phosphinic acid (yield= 64%), after which the process is performed successively, using, in each step, as starting material, the compound synthesized in the previous step, according to the operating conditions described in 1.7. (yield=85%), in 1.8. (yield= 61%), in 1.7. (yield=98%) and then in 2.3. (yield=100%).

Melting point: 165° C. (decomposition).

EXAMPLE 10

N-[3-[(Aminophenylmethyl)hydroxyphosphinyl]-2-([1,1'-biphenyl]-4-ylmethyl)-1-oxopropyl]-L-alanine Hydrobromide The process is performed according to the operating conditions described in 1.6., starting with [[[(phenylmethoxy)carbonyl]amino]phenylmethyl] phosphinic acid and ethyl 2-[(4-bromophenyl)methyl]propenoate (yield=87%), after which the process is performed successively, using, in each step, as starting material, the compound synthesized in the previous step, according to the operating conditions described in 5.4. (yield=84%), in 1.7. (yield=99%), in 1.8. (yield=60%), in 1.7. (yield=95%) and then in 2.3. (yield=80%).

Melting point: 194° C. (decomposition).

EXAMPLE 11

Phenylmethyl N-[2-[[(1-amino-2-phenylethyl)hydroxyphosphinyl]methyl]-1-oxo-3-phenylpropyl] L-phenylalaninate Trifluoroacetate 11.1. 3-[Hydroxy[2-phenyl-1-[[(tert-butoxy)carbonyl]amino]ethyl]phosphinyl]-2-(phenylmethyl)propanoic acid 3-[Hydroxy[2-phenyl-1-[[(phenylmethoxy)carbonyl]amino]ethyl]phosphinyl]-2-(phenylmethyl)propanoic acid is treated with boron tribromide according to the operating conditions described in 2.3. The hydrobromide obtained is isolated and then treated with di-tert-butyl dicarbonate in the presence of triethylamine in an organic solvent such as N,N-dimethylformamide. Water is added and the mixture is extracted with ethyl acetate. The organic phases are washed with water and dried over sodium sulphate. The product is recovered in a yield of 61%.

11.2. Phenylmethyl N- [2- [[hydroxy[2-phenyl-1- [[(tert-butoxy) carbonyl]amino]ethyl]phosphinyl]methyl]-1-oxo-3-phenylpropyl]-L-phenylalaninate 3- [Hydroxy[2-phenyl-1-[[(tert-butoxy)carbonyl]amino] ethyl]phosphinyl]-2 -(phenylmethyl)propanoic acid is treated according to the operating conditions of 1.8. The product is recovered in a yield of 72%.

11.3. Phenylmethyl N- [2- [[(1-amino-2-phenylethyl) hydroxyphosphinyl]methyl]-1-oxo- 3-phenylpropyl]-L-phenylalaninate trifluoroacetate Phenylmethyl N- [2 -[[hydroxy [2 -phenyl-1-[[(tert-butoxy) carbonyl]amino]ethyl]phosphinyl]methyl]-1-oxo-3-phenylpropyl]-L-phenylalaninate is treated with a trifluoroacetic acid/dichloromethane mixture for one hour at room temperature. The mixture is evaporated to dryness. The product obtained is precipitated from ether. The product is recovered in a yield of 98%.

Melting point: 210° C. (decomposition).

EXAMPLE 12

Phenylmethyl N-[2-[[(1-amino-2-phenylethyl) phenylmethoxyphosphinyl]methyl]-1-oxo-3-phenylpropyl]-L-phenylalaninate Formate 12.1. Phenylmethyl N-[2-[[[2-phenyl-1-[[(tert-butoxy) carbonyl]amino]ethyl]phenylmethoxyphosphinyl] methyl]-1-oxo-3-phenylpropyl]-L-phenylalaninate Phenylmethyl N-[2-[[hydroxy[2-phenyl-1-[[(tert-butoxy) carbonyl]amino]ethyl]phosphinyl]methyl]-1-oxo-3-phenylpropyl]-L-phenylalaninate is treated with benzyl alcohol (1.1 eq.) in the presence of dicyclohexylcarbodiimide and dimethylaminopyridine in tetrahydrofuran. After stirring overnight at room temperature, the mixture is filtered and then evaporated to dryness. The residue is taken up in ethyl acetate. This solution is washed 3 times with water, dried over sodium sulphate and then evaporated to dryness. The product is purified by chromatography on silica gel, eluting with a 1/9 dichloromethane/methanol mixture. The product is recovered in a yield of 60%.

12.2. Phenylmethyl N-[2-[[(1-amino-2-phenylethyl) phenylmethoxyphosphinyl]methyl]-1-oxo-3-phenylpropyl]-L-phenylalaninate formate Phenylmethyl N-[2-[[[2-phenyl-1-[[(tert-butoxy) carbonyl]amino]ethyl]phenylmethoxyphosphinyl]methyl]-1-oxo-3-phenylpropyl]-L-phenylalaninate is stirred for 2 hours in the presence of formic acid. The mixture is evaporated to dryness. The product is precipitated using diethyl ether. The product is recovered in a yield of 97%.

Melting point: 192° C. (decomposition).

EXAMPLE 13

Phenylmethyl N-[3-[(1-aminoethyl)-hydroxyphosphinyl]-2-([1,1'-biphenyl]-4-ylmethyl)-1-oxo-propyl]-L-alaninate Trifluoroacetate The process is performed according to the operating conditions described in 11.1., starting with 3-[1,1'-biphenyl]-4-yl-2-[[hydroxy[2-phenyl-1-[[(phenylmethoxy) carbonyl]amino]ethyl]methyl]phosphinyl]propanoic acid. The compound obtained is treated with phenylmethyl L-alaninate according to the operating conditions described in 11.2. (yield=61%) and then in 11.3. (yield=96%).

Melting point: 205° C. (decomposition).

The other compounds in the table are synthesized in a similar manner from appropriate starting materials.

The table which follows collates the compounds of the invention, as well as their physical properties.

When n is equal to one in this table, $R_7$ represents a hydrogen atom.

TABLE
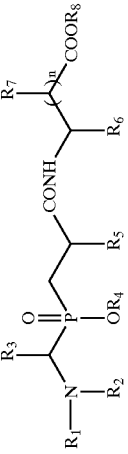
(I)
| No. | R₁ | R₂ | R₃ | R₄ | R₅ | R₆ | R₈ | n | m.p. (°C.) | Tr (min) % acetonitrile |
|-----|----|----|----|----|----|----|----|----|------------|-------------------------|
| 1 | H | H | benzyl | H | benzyl | benzyl | H | 0 | 220 (HCl) | A: 12.01<br>B: 12.8<br>C: 14.7<br>D: 22.0<br>30% |
| 2 | H | H | benzyl | H | benzyl | —CH₃ | H | 0 | 210 (HBr) | A + B: 5.4<br>C + D: 8.8<br>30% |
| 3 | H | H | benzyl | H | benzyl | —CH₂CH(CH₃)₂ | H | 0 | 230 (HBr) | A + B: 3.3<br>C + D: 7.2<br>35% |
| 4 | H | H | benzyl | H | benzyl | 4-hydroxybenzyl | H | 0 | 160 (HBr) | A + B: 8.9<br>C: 12.0<br>D: 14.2<br>25% |
| 5 | H | H | benzyl | H | benzyl | 4-phenylbenzyl | H | 0 | 170 (HBr) | A + B: 7.1<br>C: 8.8<br>D: 9.2<br>43% |
| 6 | H | H | benzyl | H | benzyl | benzyl | H | 1 | 240 (HBr) | A: 9.7<br>B: 10.3<br>C: 20.9<br>D: 25.6<br>30% |

TABLE-continued $$\begin{array}{c} R_3 \\ R_1-N \\ R_2 \end{array} \overset{O}{\underset{OR_4}{P}} \overset{R_5}{\underset{CONH}{\bigvee}} \overset{R_7}{\underset{R_6}{\bigvee_n}} COOR_8 \quad (I)$$

| No. | R₁ | R₂ | R₃ | R₄ | R₅ | R₆ | R₈ | n | m.p. (°C.) | Tr (min) % acetonitrile |
|---|---|---|---|---|---|---|---|---|---|---|
| 7 | H | H | —CH₃ | H | benzyl | benzyl | H | 0 | 230 (HBr) | A + B: 5.4  C + D: 8.8  30% |
| 8 | H | H | —CH₃ | H | 4-biphenylmethyl | benzyl | H | 0 | 175 (HBr) | A + B: 8.5  C + D: 10.9  35% |
| 9 | H | H | —CH₃ | H | 4-biphenylmethyl | —CH₃ | H | 0 | 225 (HBr) | A + B: 7.2  C + D: 10.3  30% |
| 10 | H | H | —CH₂CH₃ | H | benzyl | benzyl | H | 0 | 204 (HBr) | A + B: 6.2  C + D: 10.4  28% |
| 11 | H | H | —CH₂CH(CH₃)₂ | H | benzyl | benzyl | H | 0 | 195 (HBr) | A + B: 5.3  C + D: 7.2  35% |
| 12 | H | H | —CH₂CH₂SCH₃ | H | benzyl | benzyl | H | 0 | 175 (HBr) | A + B: 6.5  C + D: 10.4  30% |

TABLE-continued $$\begin{array}{c} R_3 \\ | \\ R_1-N \\ \quad\quad R_2 \end{array} \begin{array}{c} O \\ \| \\ P \\ | \\ OR_4 \end{array} \begin{array}{c} R_5 \\ | \\ \quad CONH \end{array} \begin{array}{c} R_7 \\ | \\ \quad\quad COOR_8 \\ R_6 \end{array}_n \quad (I)$$

| No. | R₁ | R₂ | R₃ | R₄ | R₅ | R₆ | R₈ | n | m.p. (°C.) | Tr (min) % acetonitrile |
|---|---|---|---|---|---|---|---|---|---|---|
| 13 | H | H | 4-CH₃-C₆H₄-CH₂- | H | -CH₂-C₆H₅ | -CH₂-C₆H₅ | H | 0 | 165 (HBr) | A: 10.1<br>B: 10.5<br>C + D: 12.7<br>35% |
| 14 | H | H | 2,4-(CH₃)₂-C₆H₃-CH₂- | H | -CH₂-C₆H₅ | -CH₂-C₆H₅ | H | 0 | 185 (HBr) | A + B: 16.7<br>C: 28.8<br>D: 31.9<br>30% |
| 15 | H | H | -C₆H₅ | H | -CH₂-C₆H₅ | -CH₂-C₆H₅ | H | 0 | 173 (HBr) | A: 8.25<br>B: 8.7<br>C + D: 14.0<br>30% |
| 16 | H | H | -C₆H₅ | H | -CH₂-C₆H₅ | -CH₂-C₆H₅ | H | 0 | 190 (HBr) | A + B: 3.7<br>C + D: 9.4<br>30% |
| 17 | H | H | -C₆H₅ | H | -CH₂CH(CH₃)₂ | -CH₃ | H | 0 | 150 (HBr) | A: 8.0<br>B: 8.7<br>C + D: 12.5<br>30% |
| 18 | H | H | -C₆H₅ | H | -CH₂-(4-C₆H₄-C₆H₅) | -CH₂-C₆H₅ | H | 0 | 194 (HBr) | A + B: 7.5<br>C + D: 10.4<br>33% |

TABLE-continued
| No. | R₁ | R₂ | R₃ | R₄ | R₅ | R₆ | R₈ | n | m.p. (°C.) | Tr (min) % acetonitrile |
|---|---|---|---|---|---|---|---|---|---|---|
| 19 | H | H |  | H |  |  | H | 0 | 205 (HBr) | A + B: 5.1<br>C: 5.4<br>D: 7.0<br>30% |
| 20 | H | H |  | H | —CH₂CH(CH₃)₂ |  | H | 0 | 230 (HBr) | A: 8.5<br>B: 10.1<br>C: 14.3<br>D: 15.1<br>30% |
| 21 | H | H |  | H |  | —CH₃ | H | 0 | 210 (HBr) | A + B: 15.7<br>C: 21.3<br>D: 23.2<br>30% |
| 22 | H | H |  | H |  | —CH₂CH₃ | H | 0 | 205 (HBr) | A + B: 10.0<br>C: 14.4<br>D: 15.5<br>30% |
| 23 | H | H |  | H |  | —CH₂CH(CH₃)₂ | H | 0 | 221 (HBr) | A + B: 11.4<br>C: 14.0<br>D: 14.9<br>30% |
| 24 | H | H |  | H |  |  | H | 0 | 225 (HBr) | A + B: 8.7<br>C: 10.3<br>D: 10.8<br>45% |

TABLE-continued $$\underset{R_1}{\overset{R_3}{N}}\underset{R_2}{\overset{}{\underset{}{\big|}}}\overset{}{\underset{}{\text{CH}}}-\overset{O}{\underset{OR_4}{\overset{\|}{P}}}-\overset{R_5}{\underset{}{\text{CH}}}-\text{CONH}-\overset{R_7}{\underset{R_6}{\overset{}{\underset{}{\big|}}\text{C}}}_n\text{COOR}_8 \qquad (I)$$

| No. | R₁ | R₂ | R₃ | R₄ | R₅ | R₆ | R₈ | n | m.p. (°C.) | Tr (min) % acetonitrile |
|---|---|---|---|---|---|---|---|---|---|---|
| 25 | H | H | —CH₃ | H | 4-isopropylphenyl-CH₂— | —CH₃ | H | 0 | 140 (HBr) | A + B: 7.8<br>C + D: 12.6<br>27% |
| 26 | H | H | —CH(CH₃)— | H | biphenyl-CH₂— | —CH₃ | H | 0 | 196 (HBr) | A + B: 9.2<br>C + D: 12.5<br>30% |
| 27 | H | H | benzyl | H | benzyl | benzyl | benzyl | 0 | 210* | A + B: 6.4<br>C: 7.3<br>D: 7.8<br>50% |
| 28 | H | H | benzyl | benzyl | biphenyl-CH₂— | benzyl | benzyl | 0 | 192** | A + B: 18.5<br>C + D: 21.2<br>50% |
| 29 | H | H | —CH₃ | H | biphenyl-CH₂— | —CH₃ | benzyl | 0 | 205* | B: 6.0<br>50% |

All of these compounds decompose at their melting point.
The retention times were measured by HPLC on a Chromasil column (5 μM, 100 Å, diameter: 4.6 mm, height: 250 mm), the eluent used is an acetonitrile/water (0.05% trifluoroacetic acid) mixture. The percentage of acetonitrile is given in the table.
*: (trifluoroacetate)
**: (formate)

The compounds of the invention underwent enzymological tests which allowed their inhibitory power on NEP and on APN to be determined.

Measurement of the Inhibitory Power On Neutral Endopeptidase (NEP)

The inhibitory power is determined on neutral endopeptidase purified from rabbit kidney according to the procedure described in the literature (Llorens et al., *Neurochem.*, 39, 1081, 1982). After incubation for 15 minutes at 25° C., an aliquot of proteins is incubated for 20 minutes at 37° C. in the presence of 20 nmol of ($^3$H)D-Ala$^2$-Leu$^5$-enkephalin and of the test compound dissolved in Tris-HCl buffer (pH=7.4).

The reaction is stopped by adding 0.2N hydrochloric acid. The tritiated metabolite ($^3$H)-Tyr-D-Ala-Gly is separated from the D-Ala$^2$-Leu$^5$-enkephalin by chromatography on a Porapak column and the amount of metabolite formed is measured using a liquid scintillation counter.

The activity of the various compounds of the invention, expressed as 50% inhibitory concentrations ($IC_{50}$), ranges from $10^{-6}$ to $10^{-9}$ M.

Inhibitory Power On Aminopeptidase N (APN)

The inhibitory power is measured on aminopeptidase purified from pig kidney (Boehringer, France). After preincubation for 15 minutes at 25° C., an aliquot of proteins is incubated for 20 minutes at 25° C. in the presence of 20 nmol of ($^3$H)-Leu-enkephalin and of the test compound dissolved in Tris-HCl buffer (pH=7.4).

The reaction is stopped by addition of 0.5N hydrochloric acid. The metabolite formed ($^3$H)Tyr is separated by chromatography on a Porapak column and the amount of metabolite formed is measured using a liquid scintillation counter.

The activity of the various compounds of the invention, expressed as 50% inhibitory concentrations ($IC_{50}$), ranges from $10^{-6}$ to $10^{-9}$ M.

The compounds of the invention also underwent pharmacological tests which allowed their analgesic activity to be measured.

Hot-plate Test On Mice

The test is carried out 15 minutes after intracerebroventricular administration of increasing doses of the compounds of the invention to the mice.

Two parameters are measured: the latency time for jumping and the latency time for licking.

The results are expressed as $ED_{50}$, that is to say as doses giving the half-maximal response. The analgesic activity of the various compounds of the invention are between 1 and 100 μg/kg. The activity of the most active compounds of the invention is between 1 and 20 μg/kg.

The compounds of the invention have a mixed NEP/APN activity in vitro and an analgesic activity in vivo; these results show that the compounds of the invention can be used as analgesics.

The compounds according to the invention can also be used for the preparation of drugs intended for the treatment of depressive states of any nature, sleeping disorders, anxiety disorders, cognitive disorders and disorders of alertness, and peripheral-type disorders (diarrhoea, coughing, hypertension, inflammation, etc.).

The subject of the invention is also pharmaceutical compositions comprising, as active principle, at least one of the compounds of formula (I) or one of the addition salts thereof in combination with any appropriate excipient.

The compounds of the invention can be combined with excipients, in the form of compositions formulated for enteral or parenteral administration, for example in the form of tablets, pills, granules, powders, coated tablets, wafer capsules, solutions, suspensions, injectable solutions, elixirs or syrups.

The solutions of the salts of the compounds of the invention are particularly useful for administration by intramuscular or subcutaneous injection.

The compounds of the invention are administered at a daily dose of between 0.01 and 100 mg/kg, preferably between 0.1 and 10 mg/kg.

Appendix 1

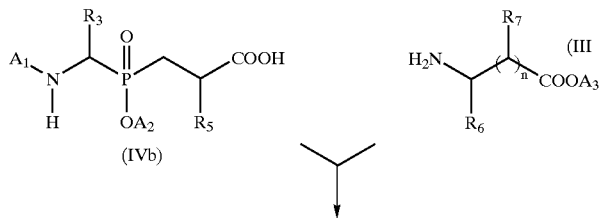

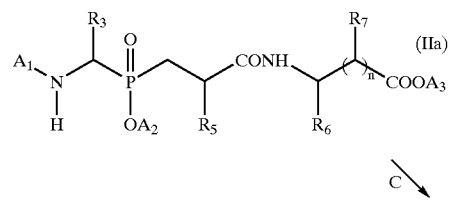

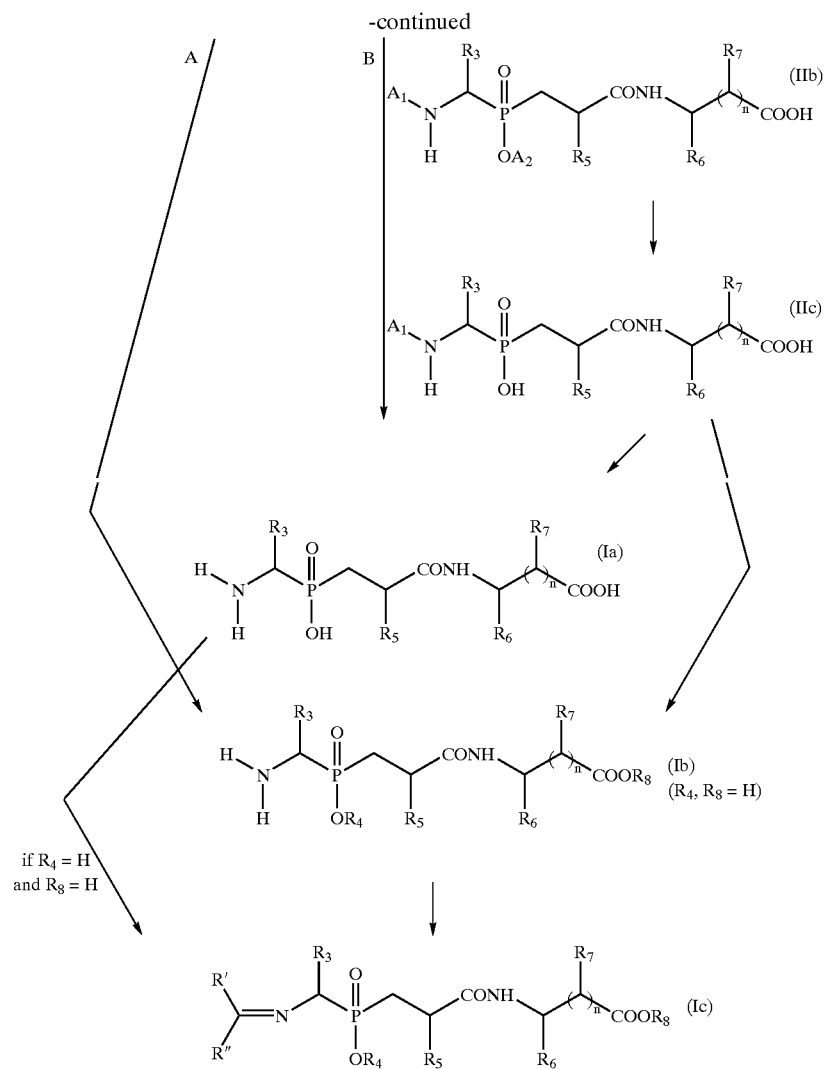
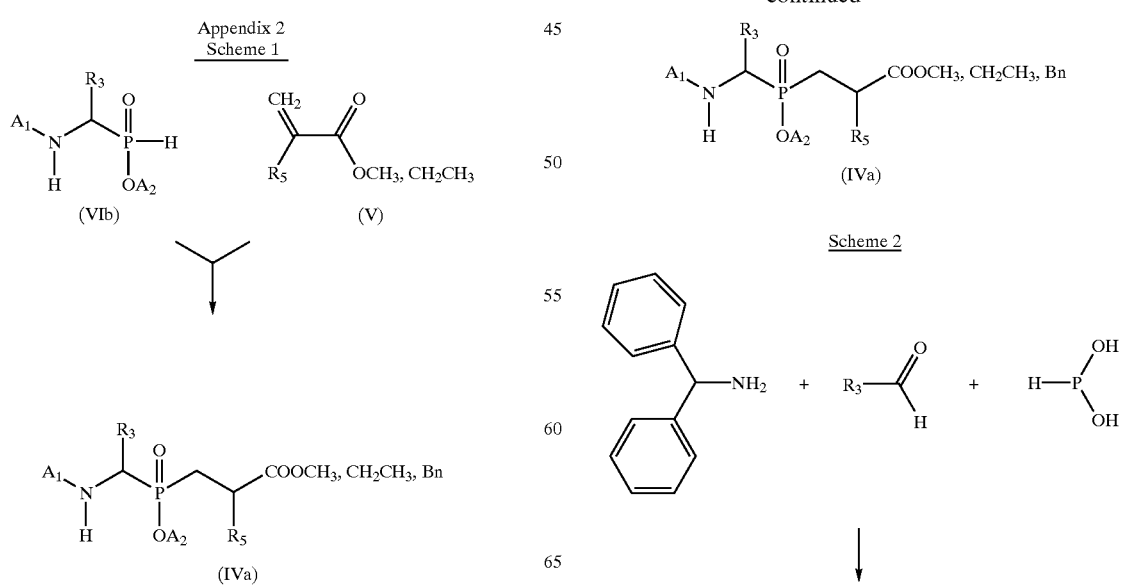

-continued

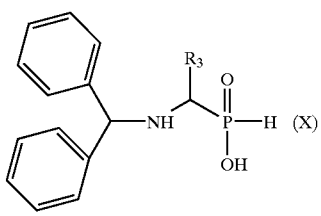

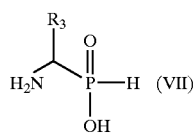

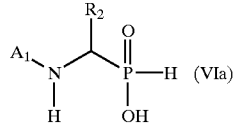

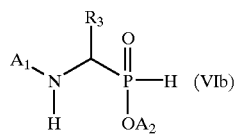

Appendix 3
Scheme 3

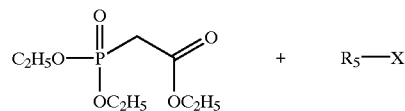

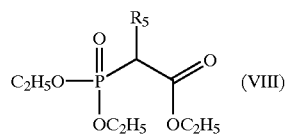

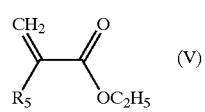

Scheme 4

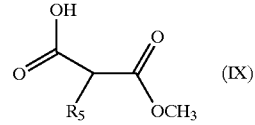

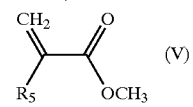

What is claimed is:

1. Compound of formula (I)

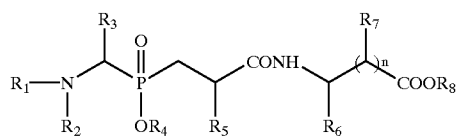

in which $R_1$ and $R_2$ each represent a hydrogen atom $R_3$ represents an alkyl group or an alkenyl group of 1 to 6 carbon atoms, it being possible for these last two groups to be substituted with:
a hydroxyl group or an alkoxy group —$OR_9$,
a phenyl group or a benzyl group,
a sulphanyl group, an alkylsulphanyl group —$SR_9$ or an alkylsulphanyl group oxidized on the sulphur atom —$S(O)R_9$,
an amino group, a group —$NHR_9$ or —$NR_9R_{10}$, optionally oxidized on the nitrogen atom, or
a guanidino group $H_2N$—$C(=NH)$—$NH$—,
a cycloalkyl or cycloalkylmethyl group,
a phenyl group, a benzyl group, which can be substituted on the phenyl group with 1 or 2 of the following substituents:
a halogen atom,
a hydroxyl group, an alkoxy group —$OR_9$,
an alkylsulphanyl group —$SR_9$ or an alkylsulphanyl group oxidized on the sulphur atom,
an amino group or a group —$NHR_9$ or —$NR_9R_{10}$ optionally oxidized on the nitrogen atom,
a nitro group,
a phenyl group,
an alkyl group of 1 to 4 carbon atoms, $R_4$ represents a hydrogen atom,
an alkyl or alkenyl group of 1 to 6 carbon atoms,
a cycloalkyl group, a cycloalkylalkyl group,
a phenyl group, a benzyl group, which can be substituted on the phenyl group with 1 or 2 of the following substituents:

an alkyl group of 1 to 6 carbon atoms,
a halogen atom,
a hydroxyl group or an alkoxy group —OR$_9$,
a trifluoromethyl group,
a nitro group, R$_5$ represents
a hydrogen atom,
an alkyl group or an alkenyl group of 1 to 6 carbon atoms, it being possible for these last two groups to be substituted with:
a hydroxyl group or an alkoxy group —OR$_9$,
a phenyl group or a benzyl group,
a sulphanyl group, an alkylsulphanyl group —SR$_9$, or an alkylsulphanyl group oxidized on the sulphur atom —S(O)R$_9$,
an amino group, a group —NHR$_9$R$_{10}$, optionally oxidized on the nitrogen atom, or
a guanidine group H$_2$N—C(=NH)—NH—,
a cycloalkyl or cycloalkylmethyl group,
a phenyl group, a benzyl group, which can be substituted on the phenyl group with 1 or 2 of the following substituents:
a halogen atom,
a hydroxyl group, an alkoxy group —OR$_9$,
an alkylsulphanyl group —SR$_9$, or an alkylsulphanyl group oxidized on the sulphur atom,
an amino group or a group —NHR$_9$ or —NR$_9$R$_{10}$ optionally oxidized on the nitrogen atom,
a nitro group,
a phenyl group,
an alkyl group of 1 to 4 carbon atoms,
a methyl group substituted with a heterocyclic group, it being possible for the hetero atoms to be oxidized in the form of N-oxide or S-oxide, R$_6$ and R$_7$ represent, independently of each other,
a hydrogen atom,
an alkyl or alkenyl group of 1 to 6 carbon atoms, which can be substituted with:
a hydroxyl group or an alkoxy group —OR$_9$,
a sulphanyl group, an alkylsulphanyl group —SR$_9$ or an alkylsulphanyl group oxidized on the sulphur atom —S(O)R$_9$,
an amino group or an alkylamino group —NHR$_9$,
a guanidine Group H$_2$N—C(=NH)—NH—, or
a carboxyl group or an alkyloxycarbonyl group —COOR$_9$
a phenyl group, a benzyl group, which can be substituted on the phenyl group by 1 or 2 of the following substituents:
a halogen atom,
a phenyl group,
a hydroxyl group or an alkoxy group —OR$_9$,
an alkylsulphanyl group —SR$_9$ or an alkylsulphanyl group oxidized on the sulphur atom —S(O)R$_9$, R$_6$ and R$_7$ together represent a saturated or unsaturated 5- or 6-membered ring comprising 1 or 2 hetero atoms, taken form among oxygen, sulphur and nitrogen, R$_8$ represents,
a hydrogen atom,
an alkyl or alkenyl group of 1 to 6 carbon atoms,
a phenyl group, a benzyl group, R$_9$ represents an alkyl group of 1 to 6 carbon atoms,
n is equal to 0 or 1,
with the exception of methyl N-[2-[[(aminomethyl)(methoxy)phosphinyl]methyl]-4-methyl-1-oxopentyl]-(1,1'-biphenyl-4-yl)-L-alaninate hydrochloride, in the form of isomers, including the form of enantiomers and diastereoisomers and mixtures of these different forms, including racemic mixtures, as well as the addition salts thereof with pharmacologically acceptable acids.

2. Compounds according to claim 1, characterized in that:

R$_1$, R$_2$, R$_4$ and R$_8$ represent hydrogen atoms, n is equal to 0,

R$_3$ represents
an alkyl group of 1 to 6 carbon atoms, which can be substituted with an alkoxy group —OR$_9$, a sulphanyl group or an alkylsulphanyl group —SR$_9$,
a phenyl group, a benzyl group, which can be substituted on the phenyl group with a halogen atom, an alkyl group of 1 to 4 carbon atoms, an alkoxy group —OR$_9$ or an alkylsulphanyl group —SR$_9$, R$_5$ represents
an alkyl group of 1 to 6 carbon atoms, which can be substituted with an alkoxy group —OR$_9$, a sulphanyl group or an alkylsulphanyl group —SR$_9$,
a phenyl group, a benzyl group, which can be substituted on the phenyl group with a halogen atom, an alkyl group of 1 to 4 carbon atoms, an alkoxy group —OR$_9$ or an alkylsulphanyl group —SR$_9$,
a biphenylmethyl group, R$_6$ represents
an alkyl group of 1 to 6 carbon atoms, which can be substituted with an alkoxy group —OR$_9$, a sulphanyl group or an alkylsulphanyl group —SR$_9$,
a phenyl group, a benzyl group, which can be substituted on the phenyl group with a halogen atom, an alkyl group of 1 to 4 carbon atoms, an alkoxy group —OR$_9$ or an alkylsulphanyl group —SR$_9$,
a biphenylmethyl group.

3. Pharmaceutical composition, characterized in that it contains a compound according to claim 2, in combination with a suitable excipient.

4. Process for the preparation of the compounds of formula (Ia)

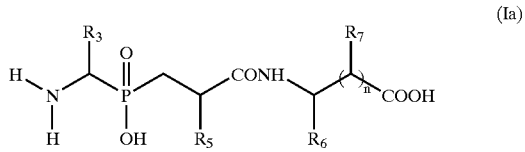

(Ia)

in which R$_3$, R$_5$, R$_6$, R$_7$ and n are as defined in claim 1, which comprises:

treating a compound of formula (IVb)

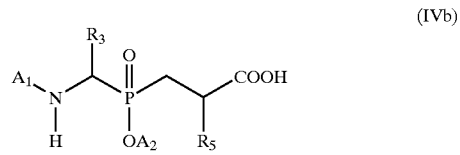

(IVb)

with a compound of formula (III)

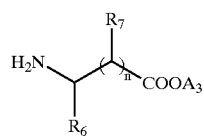
(III)

in which

A₁ represents a biphenylmethyl group, a tert-butoxycarbonyl group, a benzyloxycarbonyl group or a fluorenylmethoxycarbonyl group, A₂ represents a hydrogen atom, an alkyl group or a benzyl group, A₃ represents a methyl, ethyl, tert-butyl or benzyl group, $R_3$, $R_5$, $R_6$, $R_7$ and n are as defined in claim 1, in the presence of benzotriazol-1-yloxytris(dimethylamino)-phosphonium hexafluorophosphate, in order to obtain a compound of formula (IIa), and then in deprotecting the carboxyl, phosphinate and amine functions simultaneously or successively, and, lastly, by reaction with boron tribromide, in order to obtain a compound of formula (Ia), it being alternatively possible for this process for the preparation of the compounds of formula (Ia) to consist in deprotecting the compound of formula (IIa) directly by catalytic hydrogenation.

5. Process for the preparation of the compounds of formula (Ib)

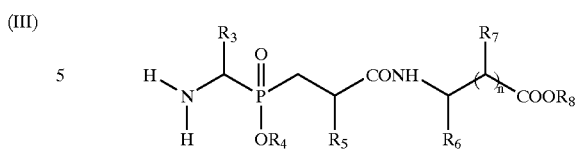
(Ib)

in which $R_3$, $R_5$, $R_6$, $R_7$ and $R_8$ and n are as defined in claim 1, with the proviso that $R_4$ and $R_8$ are other than a hydrogen atom, which comprises:

esterification of the compound of formula (IIc)

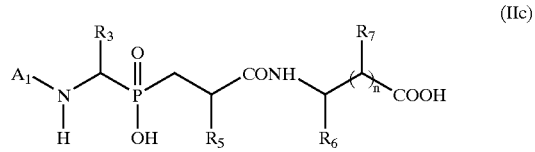
(IIc)

A₁ represents a biphenylmethyl group, a tert-butoxycarbonyl group, a benzyloxycarbonyl group or a fluorenylmethoxycarbonyl group, and $R_3$, $R_5$, $R_6$, $R_7$ and n are as defined in claim 1, followed by deprotection of the amine function, or alternatively selective deprotection of the amine function in this compound of formula (IIa) if $R_4$ and $R_8$ each represent one of an alkyl group or a benzyl group, respectively, with the exclusion of a hydrogen atom, and of methyl, ethyl, t-butyl and benzyl.

6. Pharmaceutical composition, characterized in that it contains a compound according to claim 1, in combination with any suitable excipient.

* * * * *